(12) United States Patent
Engelbart et al.

(10) Patent No.: US 7,889,907 B2
(45) Date of Patent: *Feb. 15, 2011

(54) APPARATUS AND METHODS FOR INSPECTING TAPE LAMINATION

(75) Inventors: Roger W Engelbart, St. Louis, MO (US); Reed Hannebaum, Mount Vernon, IL (US); Brian S Hensley, St. Charles, MO (US); Timothy T Pollock, Ballwin, MO (US); Samuel D Orr, Barnhart, MO (US)

(73) Assignee: The Boeing Company, Chicago, IL (US)

( * ) Notice: Subject to any disclaimer, the term of this patent is extended or adjusted under 35 U.S.C. 154(b) by 1220 days.

This patent is subject to a terminal disclaimer.

(21) Appl. No.: 11/033,779

(22) Filed: Jan. 12, 2005

(65) Prior Publication Data

US 2006/0152712 A1    Jul. 13, 2006

(51) Int. Cl.
*G06K 9/00* (2006.01)
*G01N 21/00* (2006.01)
*G01N 21/84* (2006.01)

(52) U.S. Cl. .............. 382/141; 382/111; 382/152; 356/237.1; 356/237.2; 356/429; 356/430

(58) Field of Classification Search ............ 382/111, 382/141, 152; 356/429, 430, 237.1, 237.2
See application file for complete search history.

(56) References Cited

U.S. PATENT DOCUMENTS

| | | | |
|---|---|---|---|
| 3,797,943 A | * | 3/1974 | Nagao et al. ............ 356/431 |
| 3,879,245 A | | 4/1975 | Fetherson et al. |
| 3,925,049 A | * | 12/1975 | Schwenninger ........ 65/29.18 |

(Continued)

FOREIGN PATENT DOCUMENTS

EP          0 319 797 A2     6/1989

(Continued)

OTHER PUBLICATIONS

Krupka, R et al, "Industrial Applications of Shearography for Inspection of Aircraft Components" Proceedings of the 8TH European Conference of Nondestructive Testing< Barcelona (Spain), Jun. 17-21, 2002, 'Online! Jun. 30, 2002 , XP002351899 NDT. NET—Feb. 2003, vol. 8, No. 2 Retrieved from the Internet: URL:http://www.ndt.net/articl/ecndt02/484/484.htm>'retrieved on Oct. 31, 2005.

(Continued)

*Primary Examiner*—Bhavesh M Mehta
*Assistant Examiner*—Michael A Newman
(74) *Attorney, Agent, or Firm*—Harness, Dickey & Pierce, P.L.C.

(57) ABSTRACT

A system for inspecting a composite material laid onto a substrate by a lamination machine. An imaging assembly attached to a rear portion of a delivery head of the machine obtains an image of at least a portion of the laid material beneath the imaging assembly. A processor inspects the image to detect a flaw. This system can provide an image of laid tape obtained close to a tape compaction point and can be implemented as a retrofit or as original equipment in lamination machines.

18 Claims, 6 Drawing Sheets

U.S. PATENT DOCUMENTS

| | | | |
|---|---|---|---|
| 4,064,534 | A | 12/1977 | Chen et al. |
| 4,310,132 | A | 1/1982 | Robinson et al. |
| 4,531,992 | A * | 7/1985 | Eaton .......................... 156/152 |
| 4,533,245 | A * | 8/1985 | Love, III ...................... 356/430 |
| 4,548,859 | A | 10/1985 | Kline et al. |
| 4,608,220 | A | 8/1986 | Caldwell et al. |
| 4,693,678 | A | 9/1987 | Von Volkli |
| 4,699,683 | A | 10/1987 | McCowin |
| 4,760,444 | A | 7/1988 | Nielson et al. |
| 4,780,262 | A | 10/1988 | Von Volkli |
| 4,790,898 | A | 12/1988 | Woods |
| 4,830,298 | A | 5/1989 | Van Blunk |
| 4,875,777 | A * | 10/1989 | Harding ....................... 356/606 |
| 4,877,471 | A | 10/1989 | McCowin et al. |
| 4,941,182 | A | 7/1990 | Patel |
| 4,972,326 | A * | 11/1990 | Jung et al. ..................... 702/36 |
| 5,024,399 | A | 6/1991 | Barquet et al. |
| 5,058,497 | A | 10/1991 | Bishop et al. |
| 5,120,976 | A * | 6/1992 | Clayton et al. ......... 250/559.07 |
| 5,198,983 | A | 3/1993 | Blake et al. |
| 5,337,647 | A | 8/1994 | Roberts et al. |
| 5,431,749 | A * | 7/1995 | Messner ...................... 156/358 |
| 5,439,549 | A | 8/1995 | Fryc et al. |
| 5,450,147 | A | 9/1995 | Dorsey-Palmateer |
| 5,480,508 | A * | 1/1996 | Manabe et al. ............... 156/353 |
| 5,518,208 | A | 5/1996 | Roseburg |
| 5,540,126 | A | 7/1996 | Piramoon |
| 5,562,788 | A * | 10/1996 | Kitson et al. ................... 156/64 |
| 5,651,600 | A | 7/1997 | Dorsey-Palmateer |
| 5,683,646 | A | 11/1997 | Reilling, Jr. |
| 5,700,337 | A | 12/1997 | Jacobs et al. |
| 5,746,553 | A | 5/1998 | Engwall |
| 5,804,276 | A | 9/1998 | Jacobs et al. |
| 5,814,386 | A | 9/1998 | Vasiliev et al. |
| 5,825,495 | A | 10/1998 | Huber |
| 5,871,117 | A | 2/1999 | Protasov et al. |
| 5,917,588 | A | 6/1999 | Addiego |
| 5,949,550 | A * | 9/1999 | Arndt et al. .................. 356/430 |
| 5,963,660 | A | 10/1999 | Koontz et al. |
| 5,979,531 | A | 11/1999 | Barr et al. |
| 6,012,883 | A | 1/2000 | Engwall et al. |
| 6,013,341 | A | 1/2000 | Medvedev et al. |
| 6,045,651 | A | 4/2000 | Kline et al. |
| 6,074,716 | A | 6/2000 | Tsotsis |
| 6,086,696 | A | 7/2000 | Gallagher |
| 6,112,792 | A | 9/2000 | Barr et al. |
| 6,168,358 | B1 | 1/2001 | Engwall et al. |
| 6,205,239 | B1 | 3/2001 | Lin et al. |
| 6,364,250 | B1 | 4/2002 | Brinck et al. |
| 6,369,492 | B1 | 4/2002 | Sugimoto |
| 6,390,169 | B1 | 5/2002 | Johnson |
| 6,451,152 | B1 | 9/2002 | Holmes et al. |
| 6,480,271 | B1 | 11/2002 | Cloud et al. |
| 6,648,273 | B2 | 11/2003 | Anast |
| 6,692,681 | B1 | 2/2004 | Lunde |
| 6,725,123 | B1 * | 4/2004 | Denuell ....................... 700/122 |
| 6,799,619 | B2 | 10/2004 | Holmes et al. |
| 6,814,822 | B2 | 11/2004 | Holmes |
| 6,871,684 | B2 | 3/2005 | Engelbart et al. |
| 6,914,679 | B2 * | 7/2005 | Nettekoven et al. .......... 356/430 |
| 6,961,127 | B2 * | 11/2005 | Björk .......................... 356/430 |
| 6,995,838 | B2 * | 2/2006 | Blanchard et al. .......... 356/237.2 |
| 7,171,033 | B2 * | 1/2007 | Engelbart et al. ............ 382/141 |
| 7,242,902 | B2 * | 7/2007 | Kimura et al. ............... 399/401 |
| 7,362,437 | B2 * | 4/2008 | Engelbart et al. ............ 356/430 |
| 7,424,902 | B2 * | 9/2008 | Engelbart et al. ............ 156/351 |
| 2001/0002149 | A1 | 5/2001 | Vaez-Iravani et al. |
| 2001/0023349 | A1 | 9/2001 | Van Tassel et al. |
| 2002/0141632 | A1 | 10/2002 | Engelbart et al. |
| 2003/0145932 | A1 * | 8/2003 | Holmes et al. ................. 156/64 |
| 2004/0098852 | A1 | 5/2004 | Nelson |
| 2005/0023414 | A1 | 2/2005 | Braun |
| 2005/0025350 | A1 | 2/2005 | Engelbart et al. |
| 2005/0039842 | A1 | 2/2005 | Clark et al. |
| 2005/0039843 | A1 | 2/2005 | Johnson et al. |
| 2005/0039844 | A1 | 2/2005 | Engwall et al. |
| 2006/0108048 | A1 | 5/2006 | Engelbart et al. |
| 2006/0109454 | A1 | 5/2006 | Engelbart et al. |

FOREIGN PATENT DOCUMENTS

| | | |
|---|---|---|
| EP | 0903574 | 3/1994 |
| EP | 0 833 146 A2 | 1/1998 |
| EP | 1 030 172 | 8/2000 |
| JP | 2001012930 | 1/2001 |
| WO | WO 94/18643 | 8/1994 |
| WO | WO 9418643 A1 * | 8/1994 |
| WO | WO 2004/025385 | 3/2004 |

OTHER PUBLICATIONS

Office Action Summary from the USPTO mailed Oct. 18, 2006 in reference to U.S. Appl. No. 10/846,974, filed, May 14, 2004, first named inventor Roger W. Engelbart, Art Unit 2624, Included is a list of references cited by the applicant and considered by examiner and a list of references cited by examiner.

The Written Opinion for International Application PCT/US2004/039905, dated May 25, 2005, 6 pages.

International Search Report dated May 25, 2005 for report for International Application PCT/US2004/039905, dated Nov. 30, 2004, 4 pages.

Prof. J. Zhang: "Angewandte Sensorik" Ch. 4, Sensoren in Der Robotik, Nov. 11, 2003; (retrieved from the Internet, URL:http://tech-www. Informatik.uni-hamburg nsorik/vorlesung_03.pdf) retrieved on Apr. 2004! p. 89, 20 pages.

U.S. Appl. No. 10/628,691 entitled Systems And Methods For Identifying Foreign Objects and Debris (FOD) and Defects During Fabrication of A Composite Structure, filed Jul. 28, 2003, Engelbart et al.

U.S. Appl. No. 10/717,030 entitled Method of Transferring Large Uncured Composite Lamintes, filed Nov. 18, 2003, Johnson.

U.S. Appl. No. 10/726,099 entitled Systems and Methods for Determining Defect Characteristics of a Composite Structure, filed Jul. 28, 2003, Engelbart et al.

U.S. Appl. No. 10/799,306 entitled Systems and Methods for Enabling Automated Return to and/or Repair of Defects with a Material Placement Machine, filed Mar. 12, 2004, Engelbart et al.

U.S. Appl. No. 10/819,084, filed Apr. 6, 2004, Turnmire et al.

U.S. Appl. No. 10/853,075, filed Apr. 6, 2004, Johnson et al.

U.S. Appl. No. 10/851,381 entitled Composite Barrel Sections for Aircraft Fuselages and Other Structures, and Methods and Systems for Manufacturing Such Barrel Sections, filed May 20, 2004, Biornstad et al.

U.S. Appl. No. 10/822,538 entitled Systems and Methods for Using Light to Indicate Defect Characteristics of Composite Structure, filed Apr. 12, 2004, Engelbart et al.

U.S. Appl. No. 60/559,890, Biornstad et al., filed Apr. 6, 2004.

U.S. App. No. 60/559,911, Johnson et al., filed Apr. 4, 2004.

U.S. Appl. No. 10/949,848, Stulc, filed Sep. 23, 2004.

European Search Report, Application No. 04076900.2, dated Dec. 1, 2004, 4 pages.

Fiedler, L., et al, "Tango Composite Fuselage Platform", SAMPE Journal, vol. 39, No. 1, Jan./Feb. 2003, pp. 57-63.

Advanced Technology Tape Laying for Affordable Manufacturing of Large Composite Structures; http://www.cinmach.com/tech/pdf/TapeLayingGrimshaw.pdf; Michael N. Grimshaw, et al; 11 pages (2001).

Fiber Placement; http://www.cinmach.com/tech/pdf/asm_chapter_fp.pdf; Don O. Evans; Cincinnati Machine; 3 pages (2001).

Automated Tape Laying; http://www.cinmach.com//tech/pdf/Grimshaw%20ASM%20Handbook.pdf; Michael N. Grimshaw; Cincinnati Machine; 6 pages (2001).

Raytheon Aircraft's Hawker Horizon Reaches Fuselage Milestone, Raytheon News Release; http://www.beechcraft.de/Presse/2000/100900b.htm; 2 pages (2002).

BAe 146, Flight International, May 2, 1981, 2 pages.

A Barrelful of Experience, Intervia, May 1992, 2 pages.

Raytheon, Mar. 2000, vol. 4, No. 2, http://www.cts.com/king/vasci/newsletter/vol42.html, 2 pages.

Patent Abstracts of Japan, vol. 2000, No. 16, filed May 8, 2001.

Business Aviation, Jun. 7, 2002, http://www.aviationnow.com/avnow/news/channel_busav.jsp?view=story&id=news/btoyo0607.xml, 1 page.

Beechcraft's Composit Challenge, http://www.aerotalk.com/Beech.cfm, 2 pages (Aug. 2003).

Sharp et al., "*Material Selection/Fabrication Issues for Thermoplastic Fiber Placement*", Journal of Thermosplastic Composite Materials, vol. 8; Jan. 1995, pp. 2-14.

http://www.cinmach.com/WolfTracks4.1/MTG.WTZ.htm; Premier I Features Lighter Stronger, All-Composite Fuselage, 3 pages (1998).

htpp://www.cinmach.com/compnews/PressReleases/pr00-11htm; Raytheon Aircraft Orders Four More Fiber Cincinnati Fiber Placement Systems for Industry's First Composite-Fuselage Business Jets, 2 pages (2000).

htpp://www.rockymountaincomposites.com/wind.sys.htm: Filament Winding, 2 pages (2000).

\* cited by examiner

APPARATUS AND METHODS FOR INSPECTING TAPE LAMINATION

FIELD OF THE INVENTION

The present invention relates generally to using a tape lamination machine to fabricate composite structures. More particularly, but not exclusively, the present invention relates to systems and methods for detecting and marking inconsistencies in tape laid by a tape lamination machine.

BACKGROUND OF THE INVENTION

Automated tape lamination is widely used in aerospace and other industries in the fabrication of large composite structures. A contour tape lamination machine (CTLM) may be used to lay composite tape in courses and plies onto a substrate. The tape is laid by a delivery head suspended from a gantry structure over the substrate. Tape may be applied in widths, for example, of six or twelve inches. A compaction shoe of the delivery head compacts the tape onto the substrate.

During the tape placement process, courses of laid tape typically are inspected for flaws such as gaps, overlaps and foreign objects. Visual inspection, however, can result in considerable machine down time. Inspection of taped areas close to the compaction shoe can be particularly difficult, because a typical CTLM delivery head has a low profile in relation to the substrate onto which tape is being laid. Additionally, the delivery head has a broad circumference relative to the compaction shoe. Thus the shape of the delivery head makes it difficult to find a line of sight to a compaction point for inspection purposes.

SUMMARY OF THE INVENTION

The present invention, in one implementation, is directed to a system for inspecting a composite material laid onto a substrate by a lamination machine. An imaging assembly attached to a rear portion of a delivery head of the machine is configured to obtain an image of at least a portion of the laid material beneath the imaging assembly. A processor is configured to inspect the image to detect a flaw.

In another implementation, the invention is directed to a method of inspecting composite material laid onto a substrate by a lamination machine delivery head. Movement of a paper backing of the composite material away from the material is detected. An image of the laid composite material is obtained based on the detected movement. The image is inspected to detect a flaw, and a location of the flaw is identified in the laid material.

In another configuration, a tape lamination machine includes a delivery head that lays a composite material as tape onto a substrate. An imaging assembly positioned substantially between a rear portion of the delivery head and the substrate is configured to obtain an image of the tape laid onto the substrate by the delivery head. A processor is configured to inspect the image to detect a flaw. A marking assembly behind the imaging assembly marks the laid tape to indicate the detected flaw.

In still another configuration, the invention is directed to a system for inspecting material laid as tape by a tape lamination machine onto a substrate. The system includes an imaging assembly mounted to a delivery head of the machine substantially between a rear portion of the delivery head and the substrate. The imaging assembly is configured to obtain an image of the tape laid onto the substrate by the delivery head. A processor is configured to inspect the image to detect a flaw. A marking assembly behind the imaging assembly marks the laid tape to indicate the detected flaw. A tracking wheel tracks movement of backing paper from the tape. The tracking wheel and the processor are configured to actuate at least one of the imaging and marking assemblies based on the backing paper movement.

In yet another configuration, the invention is directed to a system for inspecting output of a tape lamination machine. The system includes means for producing an image of tape placed on a substrate by a delivery head of the machine, and means for inspecting the image to detect a flaw in the placed tape. The system also includes means for identifying a location of the flaw in the placed tape, and means for detecting removal of a backing from the tape. Operation of the image producing means and the identifying means are timed based on the detecting means.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
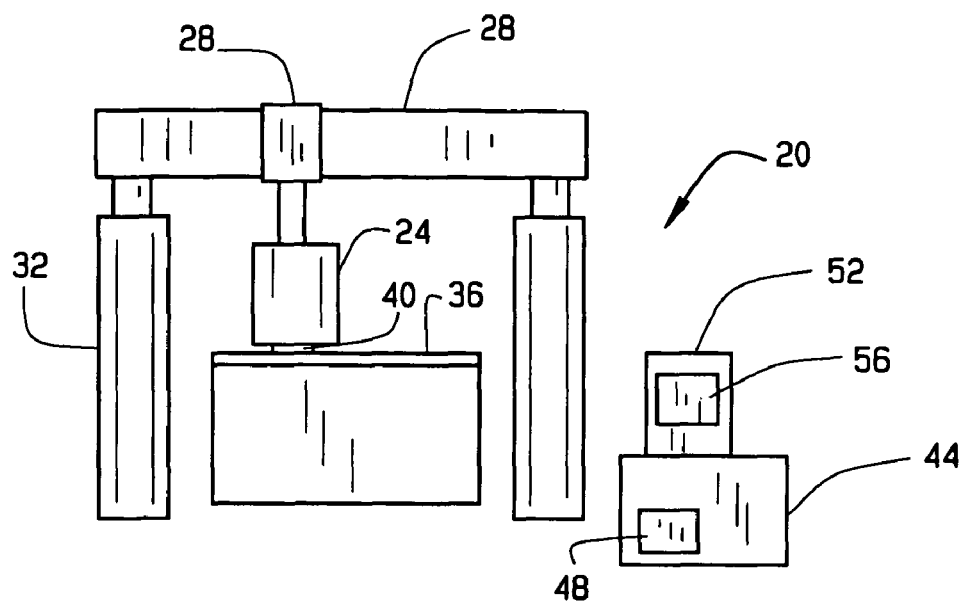
FIG. 1 is a frontal view of a contour tape lamination machine (CTLM) in accordance with one configuration of the present invention.

The following description of the preferred embodiment(s) is merely exemplary in nature and is in no way intended to limit the invention, its application, or uses. For purposes of clarity, the same reference numbers may be used in the drawings and this description to identify similar elements. The term "processor" can include but is not limited to one or more processors, computers, microcomputers, application specific integrated circuits (ASICs), electronic circuits, combinational logic circuits, and/or other suitable components that provide the described functionality. Although configurations of the present invention are described with reference to a contour tape lamination machine (CTLM), the invention is not so limited. Embodiments also are contemplated in connection with other types of lamination machines, including but not limited to flat tape lamination machines, and in connection with other automated material placement machines and processes.

An exemplary configuration of a contour tape lamination machine (CTLM) is indicated generally in FIG. 1 by reference number 20. The CTLM 20 includes a delivery head 24 suspended beneath movable parts 28 of a gantry structure 32. The CTLM 20 is used to lay down composite material in the form of tape (not shown in FIG. 1), for example, in 6-inch and/or 12-inch widths onto a substrate 36 to fabricate a composite structure. The head 24 includes a compaction shoe 40 that can be positioned over and/or onto the substrate 36. The gantry parts 28 may be moved to move the delivery head 24 relative to the substrate 36. The CTLM 20 includes a processor 44 having a memory and/or storage device 48. The processor 44 is in communication with the head 24. A user interface 52 may be, e.g., a computer monitor including a display screen 56 and an input device such as a keyboard and mouse (not shown). The user interface 52 is in communication with the processor 44.

Figure 2:
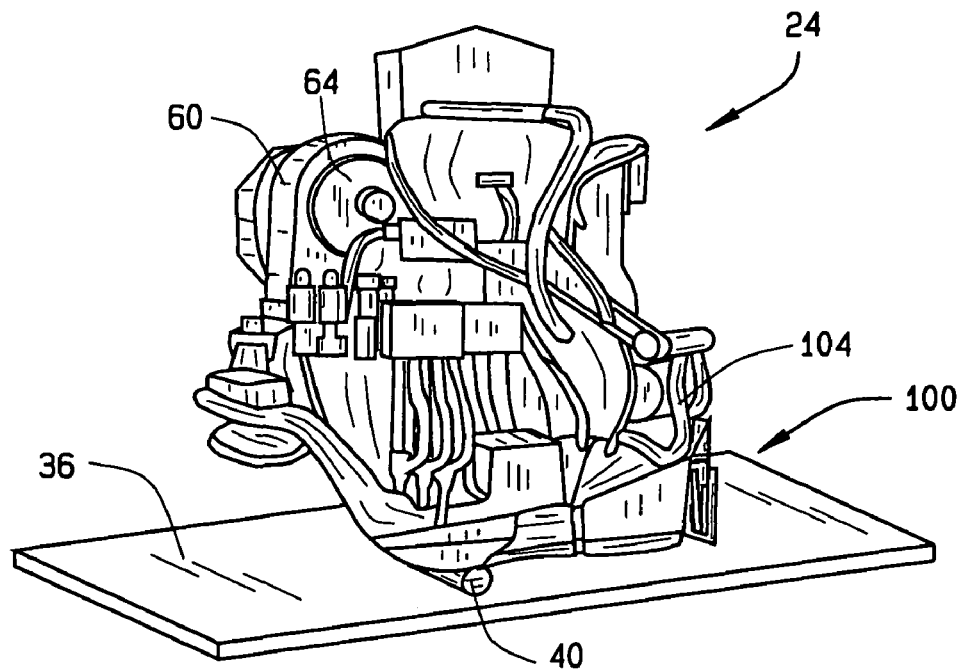
FIG. 2 is a side perspective view of a CTLM delivery head in accordance with one configuration of the present invention.
Figure 3:
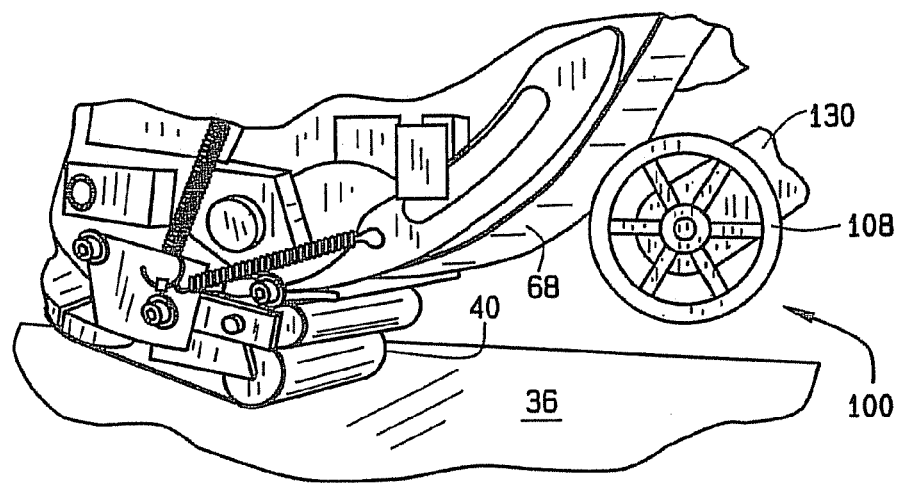
FIG. 3 is a side perspective view of part of a system for inspecting output of a contour tape lamination machine in accordance with one configuration of the present invention.
Figure 4:
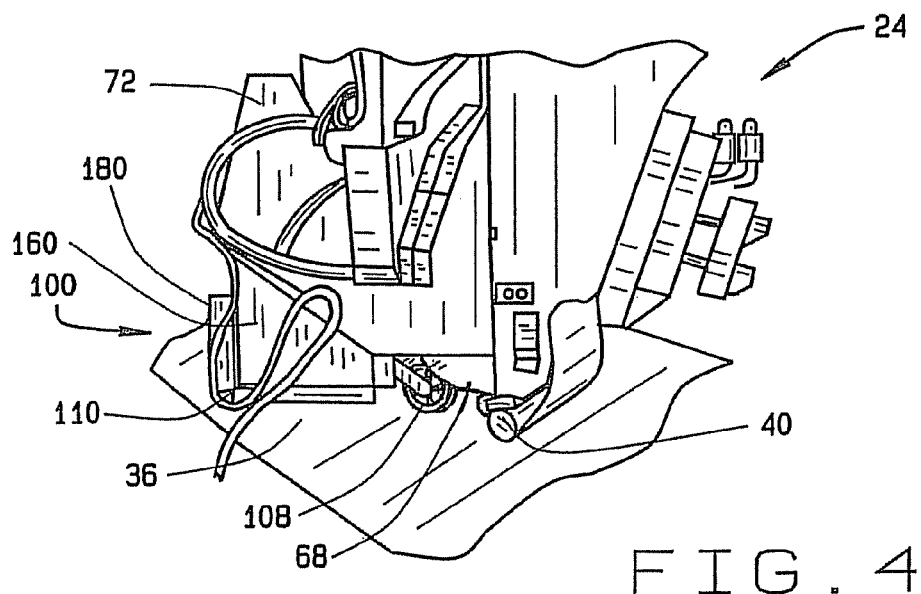
FIG. 4 is a side perspective view of a CTLM delivery head including an inspection system for inspecting output of the delivery head in accordance with one configuration of the present invention.
Figure 5:
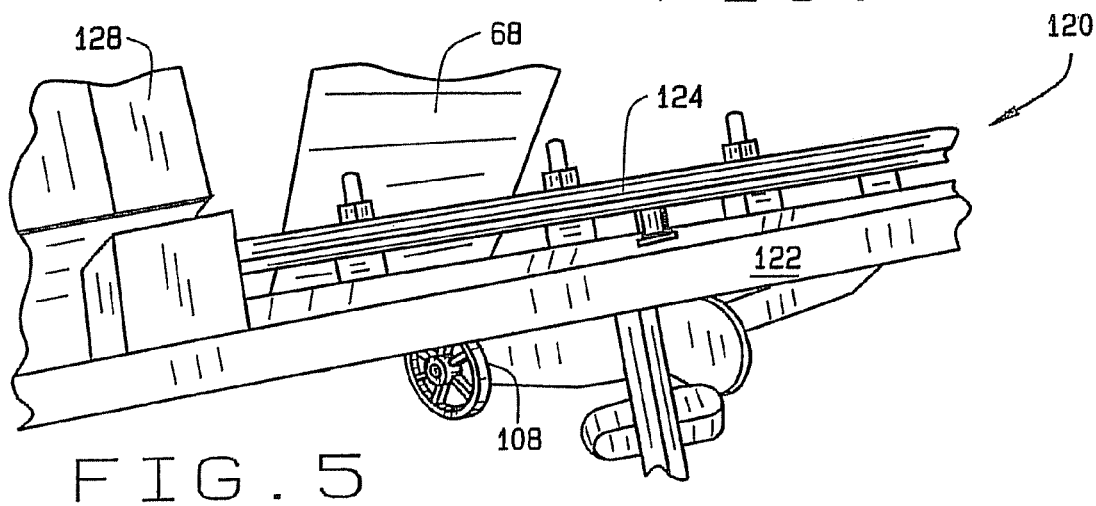
FIG. 5 is a rear perspective view of part of a system for inspecting output of a contour tape lamination machine in accordance with one configuration of the present invention.
Figure 6:
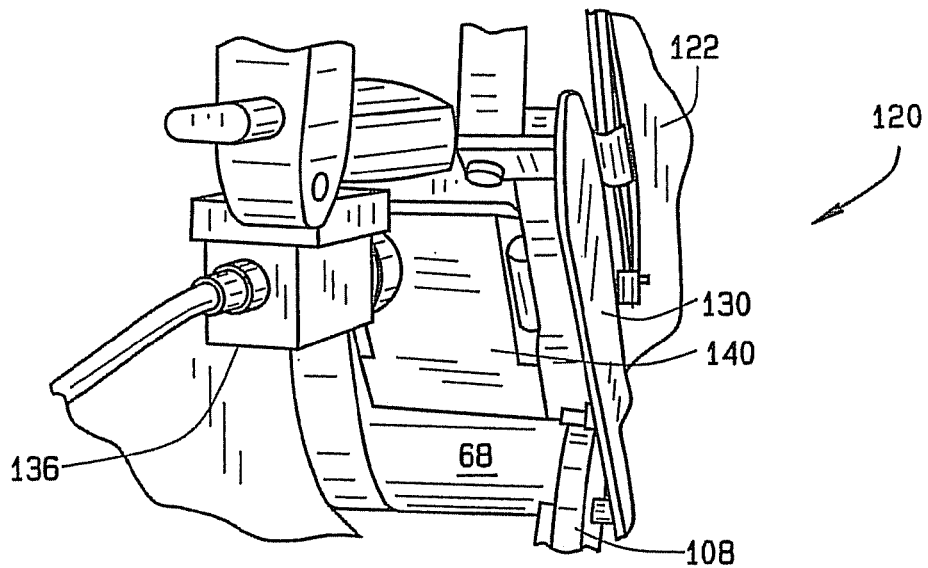
FIG. 6 is a rear perspective view of an imaging assembly in a system for inspecting output of a contour tape lamination machine in accordance with one configuration of the present invention.
Figure 7:
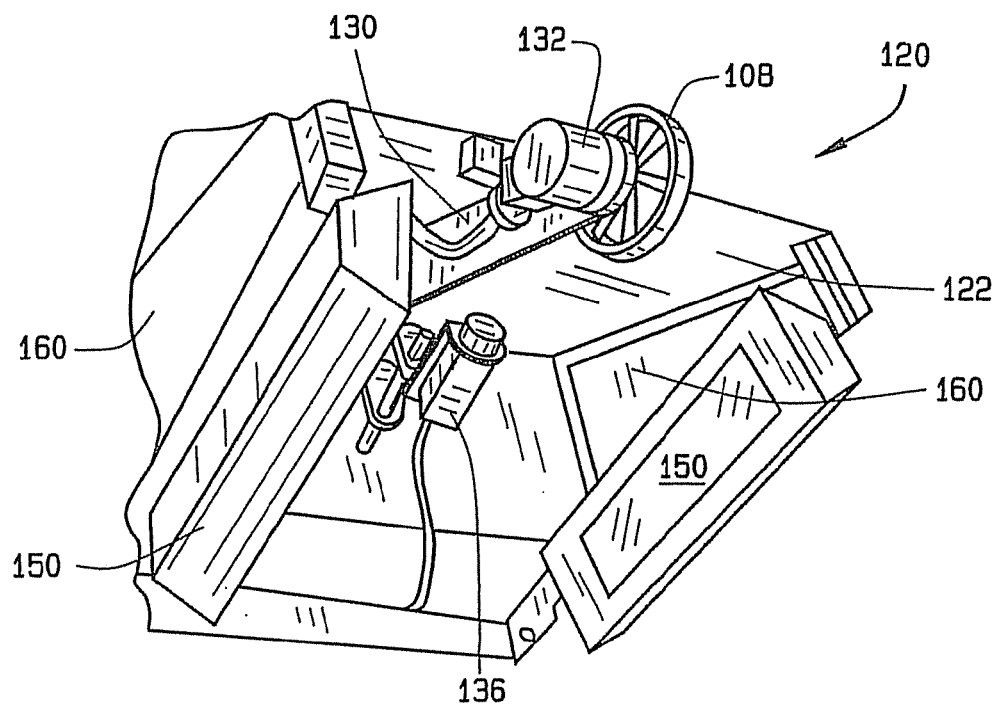
FIG. 7 is a bottom perspective view of an imaging assembly of a system for inspecting output of a contour tape lamination machine in accordance with one configuration of the present invention.
Figure 8:
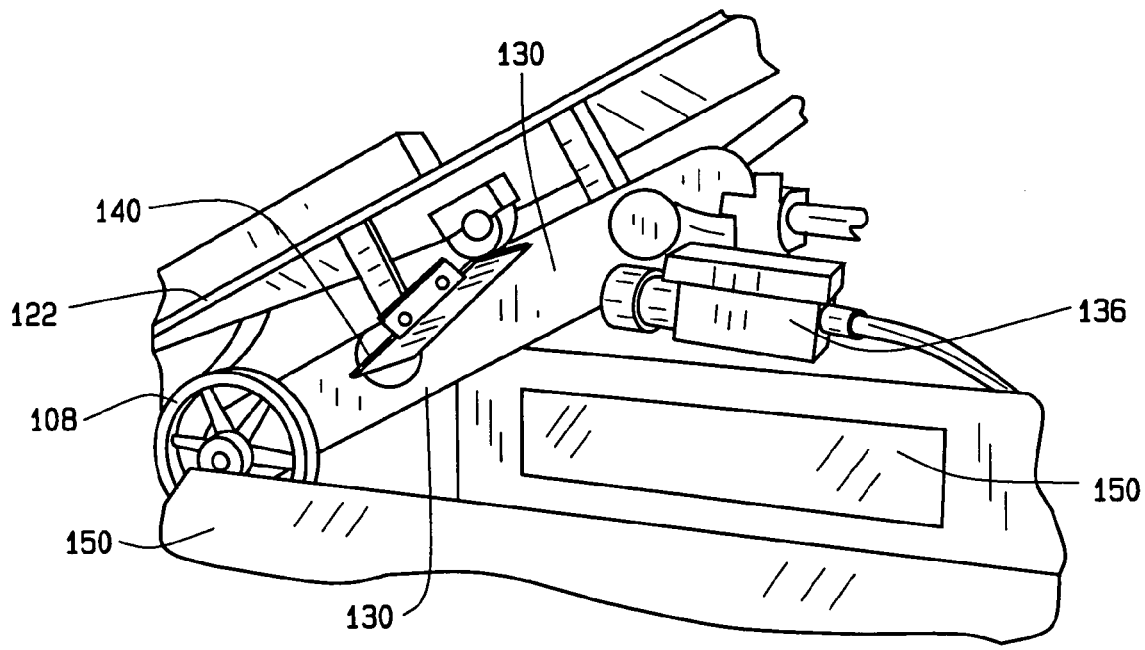
FIG. 8 is a side perspective view of part of an imaging assembly in a system for inspecting output of a contour tape lamination machine in accordance with one configuration of the present invention.

The delivery head 24 is shown in greater detail in FIGS. 2 through 4. The compaction shoe 40 is stationary relative to the head 24. A roll of composite tape 60 is mounted on a tape reel 64 above and in front of the compaction shoe 40. A surface of the tape 60 that is to be bonded to the substrate 36 is covered with a backing paper 68. As the tape 60 is advanced toward the compaction shoe 40 for application to the substrate 36, the backing paper 68 is separated from the tape 60 and wound onto a take-up spool (not shown) in a compartment 72 above and behind the compaction shoe 40. The compaction shoe 40 compacts the composite material onto the substrate 36.

A system for inspecting output of the delivery head 24 in accordance with one embodiment of the present invention is indicated generally in FIGS. 2-4 by reference number 100. The inspection system 100 can detect and mark tape inconsistencies in real time as further described below. The inspection system 100 is attached behind the compaction shoe 40 and substantially below a rear portion 104 of the head 24. The inspection system 100 includes a tracking wheel 108 in contact with the backing paper 68. The tracking wheel 108 is used to time inspection of laid tape 60 by the inspection system 100. The tracking wheel 108 is rotated by the backing paper 68 as the paper 68 is wound onto the take-up spool.

A laser proximity sensor 110 detects a distance between the head 24 and the substrate 36. The proximity sensor sends a signal representing the distance to the processor 44 for determining whether the head 24 is in contact with the substrate 36. Starting and stopping of a tape course thus can be determined by receipt of a signal from the laser proximity sensor indicating that the head 24 is in contact with the substrate 36, followed by receipt of a signal indicating that the head 24 no longer is in contact with the substrate 36. The processor 44 can track an amount of time elapsing between tape course start and stop. In the present configuration, the start of a new course can be determined without having to obtain measurements of pressure directly from the head 24. The laser sensor 110 can be positioned in an alternative location in which the sensor position is stationary and perpendicular to the substrate 36. In other configurations, other elements including but not limited to sound detectors, other laser devices, and/or pressure devices for operating the compaction shoe 40 could be used to track a tape course.

The inspection system 100 is shown in greater detail in FIGS. 5-12 and includes an imaging assembly 120. The imaging assembly 120 includes a mounting plate 122 attached, e.g., bolted, to a support bar 124. The support bar 124 is attached, e.g., welded, to a frame 128 of the head 124. The tracking wheel 108 is rotatably mounted on a bracket 130 attached to the mounting plate 122. The wheel 108 includes an encoder 132 connected with the processor 44 that tracks revolutions of the wheel 108 as the wheel is rotated by movement of the backing paper 68 as the paper is pulled by the revolving take-up spool.

A camera 136 and a reflective surface, e.g., a mirror 140, are mounted to the mounting plate 122. The mirror 140 is positioned relative to the substrate 36 to reflect an image of a region of the tape 60 that is newly laid onto the substrate 36 by the compaction shoe 40. The mirror image is reflected toward the camera 136, which communicates the reflected image of the placed tape region to the processor 44. The camera 136 has a field of view sufficiently broad to image a full width of a newly laid tape region. A wide range of cameras can be used, including commercially available cameras capable of acquiring black-and-white images. In one embodiment, the camera 136 is a television or other type of video camera having an image sensor and a lens through which light passes when the camera is in operation. Other types of cameras or image sensors can also be used, such as an infrared-sensitive camera, a visible light camera with infrared-pass filtration, a fiber-optic camera, a coaxial camera, charge-coupled device (CCD), or complementary metal oxide semiconductor (CMOS) sensor.

A pair of light sources, e.g., lighting arrays 150 positioned at sides 154 of the imaging assembly 120 illuminate the full width of the newly laid tape region. The illumination is reflected differently by inconsistencies in the composite structure than by portions of the composite structure that are inconsistency-free. Such differences in illumination can be captured in images produced by the camera 136.

In the present configuration, the lighting arrays 150 include fluorescent lights, bur other or additional types of lighting could be used. The quality and magnitude of surface illumination of the composite structure can be affected by ambient lighting and by reflectivity of the material. Accordingly, in one embodiment, one or more infrared light sources and/or light sources having an infrared component may be used to illuminate dark flaws on a dark background. In other embodiments, a strobe or stroboscopic light source, a noble gas arc lamp (e.g., xenon arc), metal arc lamp (e.g., metal halide) and/or laser (e.g., pulsed laser, solid state laser diode array and/or infrared diode laser array) could be used. Power levels and wavelengths for light source(s) 150 may depend at least in part on the speed and sensitivity of the camera 136, speed at which the tape 60 is being laid, delivery losses, and reflectivity of the material being inspected. For example, in another embodiment, wavelengths and power levels suitable for inspecting highly reflective materials may be employed.

Where lighting used in the light sources 150 is similar to ambient lighting, side and/or rear shields 160 may be mounted to the mounting plate 122. The shields 160 may be positioned to reduce or eliminate glare, spurious reflections, and/or other artifacts caused by ambient lighting that could interfere with image quality of the camera 136 and/or hinder the detection of flaws as further described below. In another configuration, a single light source may be used to illuminate the composite structure.

Figure 9:
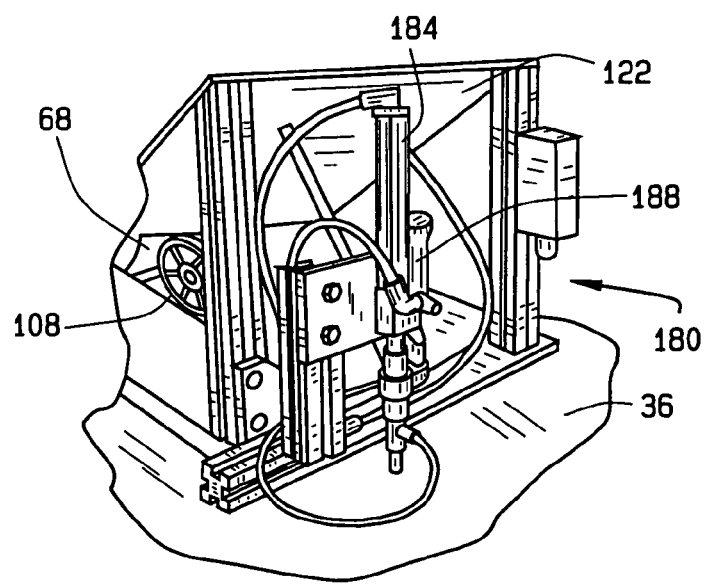
FIG. 9 is a left rear perspective view of a system for inspecting output of a contour tape lamination machine in accordance with one configuration of the present invention.
Figure 10:
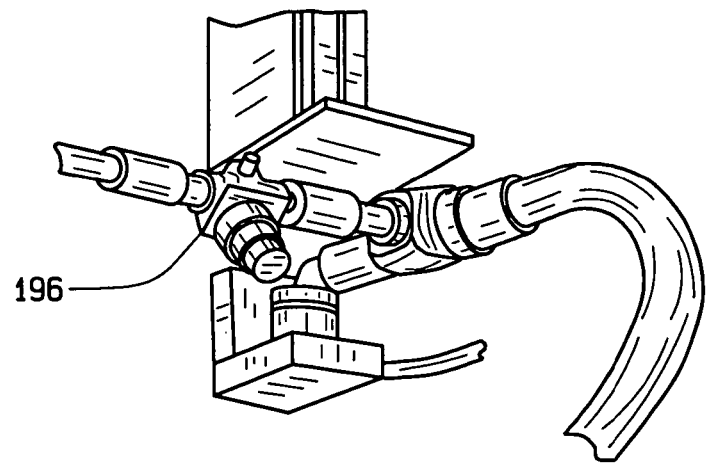
FIG. 10 is a side perspective view of a CTLM delivery head in accordance with one configuration of the present invention.
Figure 11:
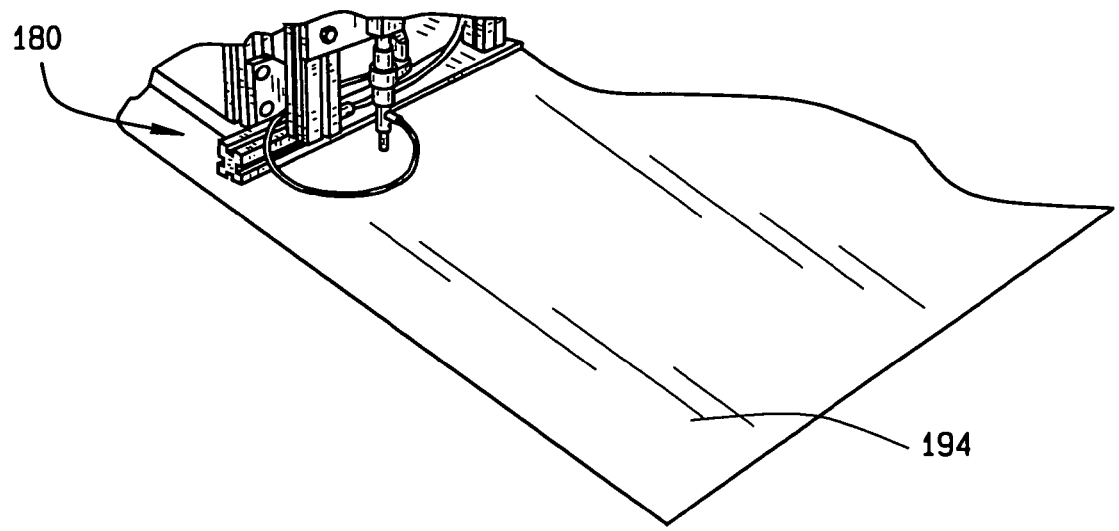
FIG. 11 is a rear perspective view of a system for inspecting output of a contour tape lamination machine in accordance with one configuration of the present invention.

The inspection system 100 includes a marking assembly, indicated generally by reference number 180 in FIGS. 9 and 11. The marking assembly 180 is mounted on the mounting plate 122 behind the imaging assembly 120. A marking plunger 184 is vertically oriented in a retracted position close to the substrate 36, for example, within about one inch of the substrate 36. In other configurations, the distance between the retracted plunger and the substrate can vary, provided that activation of the plunger causes it to reach the substrate. The plunger 184 receives ink from an ink reservoir 188. A nitrogen line 192 for pneumatically retracting and extending the delivery head 24 is used to pressurize the reservoir 188 to ensure that ink is available at the plunger 184 marker tip. A knob-operated valve 196 allows adjustment of nitrogen line pressure to the ink reservoir 188. When an inconsistency is encountered, the processor 44 may activate a solenoid (not shown) to activate the plunger 184. Exemplary marks 194 denoting inconsistencies are shown in FIG. 11. Alternatively, other marking methods could be used, including but not limited to an inkjet marking system or a spring-loaded marking pen.

When the CTLM 20 is in operation, the encoder 132 detects motion of the tracking wheel 108 caused by the backing paper 68 as it is wound onto the take-up spool. The processor 44 thereby determines that the CTLM 20 is in operation. The processor 44 actuates the camera 136 to obtain images at appropriate times based on movement of the backing paper 68 and tracking wheel 108 as the tape 60 moves through the delivery head 24. Specifically, upon completion by the tracking wheel 108 of a predetermined number of revolutions and/or partial revolutions, the processor 44 actuates the camera 132 to obtain an image of tape 60 newly placed on the substrate 36 and which is currently being reflected by the mirror 140 into the field of view of the camera 136. The processor 44 receives the image and assigns a unique number to a frame of the image data from the camera 136. The processor 44 may store image frames in the memory 48 and can use them to track a linear position of the CTLM 20 as the tape 60 is placed on the substrate 36.

The processor 44 processes the image data in a frame to detect inconsistencies in the imaged region of the tape 60. The processor 44 also analyzes and displays selected inconsistencies on the user interface 52. An inconsistency dimension, for example, a width, can be determined as follows. After a digital image of an inconsistency has been acquired, a pixel set is selected from the digital image that represents the width of the inconsistency.

The pixels in the pixel set are counted, and the count is correlated with distance to determine the inconsistency width.

Upon detection of a inconsistency, the processor 44 may actuate the marking assembly 180 to place a visually prominent ink indication next to the inconsistency. Dependent on distances and angles between elements of the imaging and marking assemblies, the processor 44 may delay the actuation of the marking assembly 180 by a predetermined time after an inconsistency is detected. Actuation may be delayed to ensure that an ink mark is applied in an appropriate location relative to the detected flaw. The processor 44 may use one or more revolutions and/or partial revolutions of the tracking wheel 108 to determine the length of such a time delay. In some configurations, relative positioning of various elements of the imaging and marking assemblies allow an inconsistency to be marked before it has moved more than an inch from the location at which it was detected.

Figure 12:
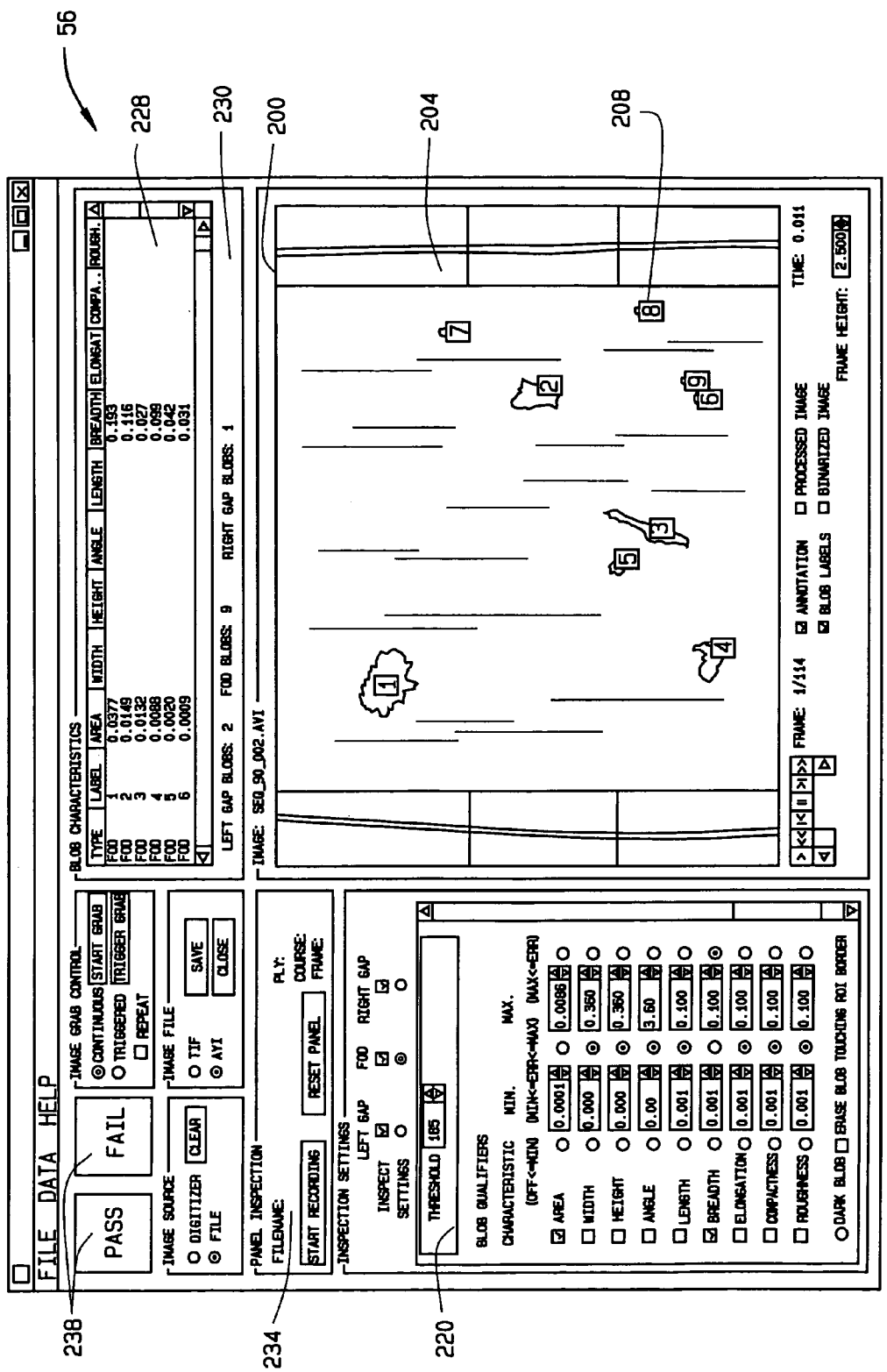
FIG. 12 is an exemplary screen shot displayed on a user interface of a system for inspecting output of a contour tape lamination machine in accordance with one configuration of the present invention.

As previously mentioned, the processor 44 may receive images from the camera 136 and/or memory 48 and may process the images to facilitate the reliable detection of inconsistency. The processor 44 may display information on the user interface display screen 56, for example, as shown in FIG. 12. A window 200 includes a frame 204 showing a region of tape imaged by the camera 136. Inconsistencies 208 (referred to as "blobs" in FIG. 12) are labeled and are shown in the window 200.

The frame 204 may include a processed or unprocessed camera image. Additionally or alternatively, the frame may include an image that has been binarized. During binarization, all shades of gray above a predetermined threshold value can be changed to white, while all gray shades below the threshold are changed to black to heighten the contrast of inconsistencies and improve the accuracy of inconsistency detection. In other embodiments, the binarization operation need not be performed but instead the raw image, rates of change of the light levels in the raw image, and/or color changes in the images can be used to identify the inconsistencys.

The user interface 52 may also allow the user to adjust or shift the viewing area within the window 200. During operation, the window 200 may display real-time moving video images of an inspected portion of a composite structure as the camera 136 and/or the reflective surface 140 are moved relative to the composite structure.

The interface 52 may allow the user to input a number of tape plies to be inspected, a number of courses to be laid per ply, and a number of image frames per course based on a viewing area size established for the camera 136. The interface 52 also may allow a user to select various inconsistency characteristics via a window 220 and also to input characteristic ranges to be applied to the display of inconsistencies during an inspection process. Such characteristics may include, for example, inconsistency area and breadth, shown in FIG. 12 as having been selected. Selected characteristics of displayed inconsistencies may be listed in a window 228. The display screen 56 can also provide information as to numbers of inconsistencies (which can be continuously updated) in an area 230 and information in an area 234 describing a ply, course and frame being inspected. Status areas 238 may display whether a particular image area is acceptable or unacceptable based, for example, on criteria predefined by the user via the interface 52.

Configurations of the foregoing inspection system can be implemented as retrofits or as original equipment in lamination machines. Configurations of the foregoing system can provide an image of laid tape obtained very close to the point of tape compaction. Additionally, inconsistencies can be detected and marked in real time during the taping process. Laminating machine down time thus can be greatly reduced or eliminated.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A system for inspecting composite tape laid onto a substrate by a tape lamination machine, the system comprising:
   an imaging assembly attached to and substantially below a rear portion of a delivery head of the tape lamination machine, and moving with the delivery head, and configured to obtain an image of a full width of the laid tape beneath the imaging assembly in real time after the tape is laid, the image obtained using a field of view oriented parallel to a direction in which the lamination machine moves across the substrate when laying the tape;
   a pair of generally opposed light sources that are supported to move with the delivery head so as to illuminate the full width of the laid tape in real time after the tape is laid, the pair of generally opposed light sources further being configured to direct light generally transversely relative to the field of view of the imaging assembly, onto the area of the laid tape to provide an ambient light for illuminating the area of the laid tape to assist the imaging assembly in obtaining the image; and
   a processor configured to inspect the image to detect a foreign object on the area of the laid tape.

2. The system of claim 1, wherein the imaging assembly is further configured to obtain the image as one of a plurality of images, wherein the plurality of images comprise real-time moving video images, the processor further configured to display the real-time moving video images on a display of the system.

3. The system of claim 1, further comprising a tracking wheel that tracks movement of backing paper from the composite tape, the tracking wheel and the processor configured to actuate the imaging assembly based on the backing paper movement.

4. The system of claim 1, wherein the imaging assembly comprises:
   a reflective surface in the field of view and supported to move with the delivery head, and upon which an incident image of the laid tape area is incident; and
   a camera supported to move with the delivery head and being configured to receive, in the field of view, the image as reflected by the reflective surface.

5. The system of claim 1, further comprising a marking assembly that marks the laid tape to indicate the detected foreign object.

6. The system of claim 5, further comprising a tracking wheel that tracks movement of backing paper from the composite tape, the processor configured to actuate the marking assembly after a delay predetermined by the processor based on revolution of the tracking wheel and locations of the imaging and marking assemblies relative to the detected foreign object.

7. The system of claim 5, wherein the marking assembly comprises a plunger that applies ink to the composite tape.

8. A method of inspecting composite tape laid onto a substrate by a tape lamination machine delivery head, the method comprising the steps of:
   detecting movement of a paper backing of the composite tape away from the tape, the detecting performed by an inspection system using a tracking wheel moved by the backing paper;
   illuminating the laid composite tape with ambient light from two ambient light sources that move with the delivery head, and which provide ambient light on the laid composite tape in two opposed directions generally transverse to the direction in which the lamination machine travels across the substrate when laying the tape;
   obtaining an image using an image sensing system that is oriented to image along a path parallel to a direction of movement of the tape lamination machine, so as to image an area including a full width of the laid composite tape using a field of view oriented parallel to the direction in which the lamination machine travels over the substrate when laying the tape, the obtaining performed by an imaging assembly of the inspection system based on the detected movement, the imaging assembly mounted substantially below a rear portion of the delivery head so as to move with the delivery head and to follow the laid composite tape;
   inspecting the image to detect a foreign object on the area of the laid composite tape; and
   identifying a location of the foreign object.

9. The method of claim 8, wherein identifying a location of the foreign object comprises:
   based on movement of the tracking wheel and on relative locations of the imaging assembly and a marking assembly mounted behind the imaging assembly, a processor of the inspection system determining a delay time after which to actuate the marking assembly;
   marking the laid composite tape to indicate the detected foreign object, the marking performed by the marking assembly; and
   displaying the image and the detected foreign object, the displaying performed using a user interface of the lamination machine.

10. The method of claim 8, wherein obtaining an image of the laid composite tape comprises:
    illuminating the laid composite tape using the two ambient light sources, wherein the two ambient light sources are further arranged to generally face one another; and
    imaging the illuminated laid composite tape using a camera of the imaging sensing system.

11. A tape lamination machine comprising:
    a delivery head that lays a composite material as tape, thus forming a tape laid, onto a substrate using a compaction shoe;
    an imaging assembly positioned substantially between a rear portion of the delivery head and the substrate, and carried with the delivery head, the imaging assembly including:
      a mirror positioned to reflect an image of a full width of the tape laid onto the substrate by the delivery head, the reflected image being obtained along a field of view oriented parallel to the direction in which the tape lamination machine moves across the substrate;
      a pair of opposed light sources carried by the delivery head so as to be moveable therewith, the opposed light sources illuminating with ambient light the tape laid by the delivery head generally below the field of view, and generally alongside opposed edges of the tape laid, which is being imaged;
    a camera carried with the delivery head for capturing the reflected image of the full width of the tape laid in real time after the tape is laid onto the substrate;
    a processor that analyzes the captured image to detect a foreign object; and
    a marking assembly supported adjacent to the imaging assembly that marks the tape laid adjacent a location where the foreign object is detected, to indicate the presence of the foreign object.

12. The machine of claim 11, further comprising a tracking wheel movable by backing paper moving away from the tape, the processor actuating at least one of the imaging and marking assemblies based on the backing paper movement.

13. The system of claim 11, wherein the marking assembly comprises a plunger that applies ink to the tape laid to indicate the foreign object, after a delay predetermined by the processor based on the backing paper movement.

14. A system for inspecting material laid as tape by a tape lamination machine onto a substrate, the system comprising:
   an imaging assembly having a mounting plate mounted to a delivery head of the machine, the imaging assembly having a camera and a reflective surface each extending from the mounting plate substantially between a rear portion of the delivery head and the substrate, the camera having a field of view oriented generally horizontally toward the reflective surface, the reflective surface oriented toward an area of the tape laid onto the substrate, the imaging assembly configured to:
      illuminate the tape laid onto the substrate by the delivery head, the illumination being ambient lighting produced by a pair of light sources at opposite sides of the mounting plate, the mounting plate having side shields mounted thereon, each said side shield extending at least between a corresponding side edge of the mounting plate and a corresponding one of the light sources; and
      obtain an image of the tape laid, the image oriented longitudinally relative to the laid tape;
   a processor configured to inspect the image to detect a foreign object;
   a marking assembly mounted to the mounting plate and behind the imaging assembly that marks the laid tape to indicate the detected foreign object; and
   a tracking wheel that tracks movement of backing paper from the tape, the tracking wheel and the processor configured to actuate both the imaging and marking assemblies based on the backing paper movement.

15. A system for inspecting output of a tape lamination machine, the system comprising:
   means for illuminating a portion of tape placed on a substrate by a delivery head of the machine, the illuminating means being carried by the delivery head and providing ambient light directed generally laterally relative to a laid portion of the placed tape along a full width of the placed tape;
   camera means carried by the delivery head for capturing an image of the laid portion of the placed tape in real time after the laid portion is laid by the delivery head, the image taken by arranging a field of view of the camera parallel to a direction along the substrate in which the tape is being laid, the field of view of the camera also being directed toward a reflecting means carried by the delivery head and angled toward the laid portion of the placed tape, wherein the reflecting means is oriented to reflect an image of the tape being laid along a path parallel to the direction in which the tape is being laid;
   means for inspecting the image to detect a foreign object relative to the placed tape;
   means for identifying a location of the foreign object relative to the placed tape; and
   means for detecting removal of a backing from the tape;
   wherein operation of the image producing means and the identifying means are timed based on the detecting means.

16. The system of claim 15, wherein the illuminating means comprises means for shielding the placed tape from light other than light produced by the illuminating means.

17. The system of claim 15, wherein the detecting means comprises an encoder wheel rotatably mounted in contact with the backing.

18. The system of claim 15, wherein the identifying means comprises at least one of:
   means for marking a location of the foreign object on the placed tape; and
   means for displaying the image and the foreign object.

* * * * *